United States Patent [19]
Ross et al.

[11] Patent Number: 5,203,784
[45] Date of Patent: Apr. 20, 1993

[54] BIOABSORBABLE TACK FOR JOINING BODILY TISSUE AND APPARATUS FOR DEPLOYING SAME

[75] Inventors: Randall D. Ross, Largo, Fla.; Stephen J. Snyder, Tarzana, Calif.; Sam R. Marchand, Dunedin, Fla.

[73] Assignee: Linvatec Corporation, Largo, Fla.

[21] Appl. No.: 753,843

[22] Filed: Sep. 3, 1991

Related U.S. Application Data

[62] Division of Ser. No. 404,378, Sep. 8, 1989, Pat. No. 5,129,906.

[51] Int. Cl.$^5$ ............................. A61F 1/04; A61F 2/08
[52] U.S. Cl. ........................................ 606/104; 606/77; 606/72; 623/13
[58] Field of Search ............... 606/104, 103, 77, 73; 623/16, 13

[56] References Cited

U.S. PATENT DOCUMENTS

| | | |
|---|---|---|
| 204,913 | 6/1878 | Pratt . |
| 2,267,925 | 12/1941 | Johnston ................................. 606/73 |
| 2,551,840 | 4/1951 | Taylor . |
| 3,103,926 | 9/1963 | Cochran et al. ...................... 606/104 |
| 4,060,089 | 11/1977 | Noiles . |
| 4,299,021 | 11/1981 | Williams . |
| 4,320,544 | 3/1982 | Bryant et al. . |
| 4,415,111 | 11/1983 | McHarri et al. . |
| 4,438,769 | 3/1984 | Pratt et al. . |
| 4,507,817 | 4/1985 | Staffeld . |
| 4,924,865 | 5/1990 | Bays et al. ............................. 606/77 |
| 4,976,715 | 12/1990 | Bayo et al. ............................. 606/77 |

Primary Examiner—David Isabella

[57] ABSTRACT

A cannulated bioabsorbable tack has annular ribs configured to enhance fixation to invivo tissue and is particularly effective for attaching soft tissue to bone, such as ligaments or muscles. Apparatus including a trocar wire, an inserter and an impactor facilitates arthroscopic surgical procedures for inserting the tack invivo to attach or join the tissue.

18 Claims, 4 Drawing Sheets

BIOABSORBABLE TACK FOR JOINING BODILY TISSUE AND APPARATUS FOR DEPLOYING SAME

This is a divisional application of application Ser. No. 07/404,378, filed Sept. 8, 1989 now U.S. Pat. No. 5,129,906.

BACKGROUND OF THE INVENTION

1. Field of the Invention

The present invention relates to repair of bodily tissue in vivo and, more particularly, to method and apparatus for attaching soft tissue to bone during arthroscopic surgery of the shoulder and to a bioabsorbable tack therefor.

2. Discussion of the Prior Art

In open surgery a large incision is required to gain access to a surgical site causing increased trauma, long periods of immobilization and, consequently, long periods of rehabilitation and recovery. The disadvantages of open surgery are particularly troublesome in joint surgery, or arthrotomies, and more particularly in reattaching torn or severed soft tissue, such as ligaments or muscles, to bone in the shoulder.

Previous systems employed to reattach separated tissue to bone have utilized metal screw and washer combinations or metal staples. The use of metal fasteners necessitates surgical procedures for fastener insertion and in some cases for fastener removal. Other disadvantages from the use of prior art fasteners are that threaded screws have a propensity to back out from their implantation position, the screw heads and washers protrude from the attachment site creating a possible source of irritation to tissue in the body, and staples must necessarily be so sharp that they do not hold or anchor well in the bone and are subject to disengagement and bending.

SUMMARY OF THE INVENTION

Accordingly, it is a primary object of the present invention to overcome the above mentioned disadvantages of the prior art by providing method and apparatus simplifying the attachment of tissue to bone and a bioabsorbable tack for securing the tissue to the bone.

Another object of the present invention is to provide a method and apparatus for arthroscopically attaching bodily tissue to bone in vivo.

The present invention has a further object in the configuration of a cannulated bioabsorbable tack for longitudinal insertion in bone with breakage or undesired deformation.

An additional object of the present invention is to construct a bioabsorbable tack with annular ribs having maximum diameter sections with cylindrical configurations to provide structural integrity and prevent breakage when inserted in hard tissue, such as bone.

A further object of the present invention is to dispose securing elements, such as internal threads, in a head of a bioabsorbable tack to reinforce the tack during insertion with a impactor having a distal end connected with the securing elements.

In accordance with the present invention, a bioabsorbable tack is designed for surgical utilization, particularly in arthroscopic surgery, to repair severed or torn tissue by re-attaching the tissue to bone. The tack is generally T-shaped with a head attached to a stem and has a longitudinal axial bore therethrough and a plurality of annular ribs along the stem. The surgical procedure for tissue repair includes insertion of a trocar wire through a portal in the skin or through an insertion cannula. The trocar wire is utilized in combination with an inserter barb to engage or hook the separated tissue and move the tissue to an attachment site against the bone, and the sharpened end of the trocar wire is driven through the tissue into the bone to serve as a guide. The repair tack is mounted on the end of an impactor by cooperating securing elements located at the distal end of the impactor and along the inner axial bore in the head of the tack to provide a continuous axial bore through the impactor and tack. The combined impactor and tack are inserted into the cannula by sliding the continuous axial bore over the embedded trocar wire until the distal end of the tack comes into contact with the tissue. The tack is then longitudinally driven into the bone by hammering the impactor until the head of the tack affixes the tissue firmly against the bone. The annular ribs on the stem of the tack firmly secure the tack in position in the bone while the impactor is disengaged from the tack and removed from the cannula. The trocar wire is then removed from the bone and the cannula. The tack is made from a bioabsorbable polymer or copolymer selected in accordance with desired degradation time and anticipated time for healing the torn or severed tissue. A plurality of tacks may be utilized to secure the torn or severed tissue at different locations.

Other objects and advantages of the present invention will become apparent from the following description of the preferred embodiment taken in conjunction with the accompanying drawings.

DESCRIPTION OF THE PREFERRED EMBODIMENT

A repair tack 10 for attachment of soft tissue to bone, in vivo, according to the present invention is illustrated in FIGS. 1 through 4. While the present invention is particularly advantageous for arthroscopic surgery and is described as deployed in the shoulder, the repair tack can be deployed to attach tissue in other areas of the body, such as in the hand, wrist, elbow, ankle, or the like and can be utilized during open surgery as well as arthroscopic or endoscopic surgery. The repair tack 10 is preferably fabricated as an integrally molded unit from suitable rigid or semi-rigid bioabsorbable or biodegradable plastic material chosen in consideration described hereinbelow; however, the tack can be formed by any suitable process, such as machining or injection molding. The tack has a proximal end 12 and a distal end 14 with a longitudinal bore 16 extending axially through the entire length of the tack 10. Most of the length of the tack 10 is occupied by a stem 18 extending rearwardly from distal end 14 to join a head 20 disposed at proximal end 12. A plurality of annular ribs 22 are disposed in axial sequence along the periphery of the stem 18. The head 20 is circular having rounded or radiused edges 21 to present no sharp edges, and the head extends transversely from the longitudinal axis 23 of the tack.

Figures 2, 4:
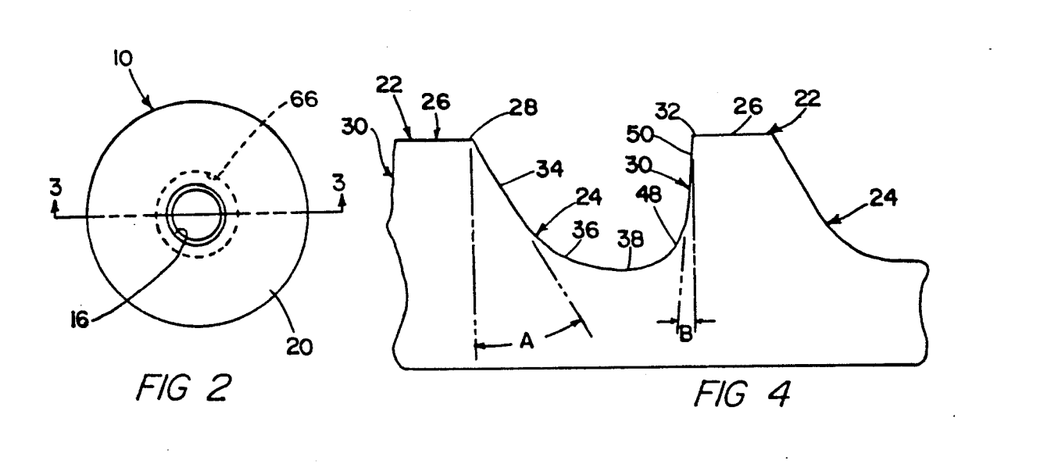
FIG. 2 is a proximal end view of the tack of FIG. 1.
FIG. 4 is a broken side view of annular ribs of the tack of FIG. 1.

As shown in FIG. 4, each annular rib 20 has a forward facing surface 24 intersecting a maximum cylindrical section 26 at a distal rib edge 28 and a rearward facing surface 30 intersecting the maximum cylindrical section 26 at a proximal rib edge 32. The forward facing surface 24 is formed of a forward frusto-conical section 34 and a forward hypercycloid section 36. The root of the stem is formed of a cylindrical section 38 having the minimum diameter of the stem 18 connecting adjacent annular ribs. Each forward frusto-conical section 34 extends from a distal rib edge 28 to a proximal end of a forward hypercycloid section 36. Each forward hypercycloid section 36 in turn extends from a distal end of a forward frusto-conical section 34 to a proximal end of the root cylindrical section 38. Each root cylindrical section 38 extends from a distal end of a forward hypercycloid section 36 to the proximal end of a rearward facing surface 30. The rearward facing surface 30 of each annular rib 22 extends from the distal end of the root cylindrical section 38 of the forward facing surface 24 of the previous proximal annular rib 44 to the proximal rib edge 32 of the subsequent distal annular rib 46. The rearward facing surface 30 of each annular rib 22 is formed of a rearward hypercycloid section 48 extending from the distal end of the root cylindrical section 38 to the proximal end of a rearward frusto-conical section 50 which in turn extends to the proximal rib edge 32.

The maximum cylindrical section 26 of each annular rib 22 forms a cylindrical structure coaxial with bore 16 and longitudinal axis 23. The width of each maximum cylindrical section 26 from the proximal rib edge 32 to the distal rib edge 28 is approximately 0.018 inches, and the length of maximum cylindrical section 26 form a flat, smooth cylindrical surface and increases the strength of the ribs to withstand the longitudinal impacting force exerted during insertion of the tack 10 into bone. The diameter of each maximum cylindrical section 26 is approximately 0.180 inches. The forward frusto-conical section 34 of each annular rib 22 is coaxial with the bore 16 and forms an angle A relative to a line transverse to the longitudinal axis 23 of approximately 30° to facilitate movement of the tack forwardly into the bone. The forward hypercycloid section 36 of each annular rib 22 is also coaxial with the bore 16, and the circular curvature of the forward hypercycloid section 36 preferably has the arc of a circle having approximately a 0.025 inch radius with a center positioned approximately 0.033 inches forwardly of the distal rib edge 28 and 0.025 inches above the root cylindrical section 38. The root cylindrical section 38 between annular ribs 22 forms a cylindrical structure coaxial with the bore 16, and the preferred diameter of the root cylindrical section 38 is approximately 0.120 inches. The rearward hypercycloid section 48 of each annular rib is coaxial with the bore 16 of the tack 10 and has a circular curvature, preferably the arc of a circle having approximately a 0.013 inch radius with a center positioned 0.0145 inches rearwardly of the proximal rib edge 32 and 0.013 inches above the root cylindrical section. The rearward frusto-conical section 50 of each annular rib 22 is coaxial with the bore 16 of the tack and preferably forms an angle B relative to a line transverse to the longitudinal axis 23 at distal rib edge 32 of approximately 5 to prevent rearward movement of the tack from the bone. The distance between proximal rib edges 32 of adjacent annular ribs 22 is approximately 0.069 inches. The diameter of the bore 16 through the tack 10 is approximately 0.071 inches, and the head 20 of the tack 10 has a diameter of approximately 0.276 inches. The securing head 20 has a proximal surface 52 extending perpendicularly to the longitudinal axis 23 and a distal surface 58 parallel to the proximal surface 52 and spaced approximately 0.060 inches therefrom, the distal surface 58 arcuately curving into a proximal end 60 of the stem 18 having a cylindrical configuration curving into the most proximal annular rib 22. The proximal end 60 of the stem has a length of approximately 0.080 inches and a diameter of approximately 0.136 inches.

Figure 3:
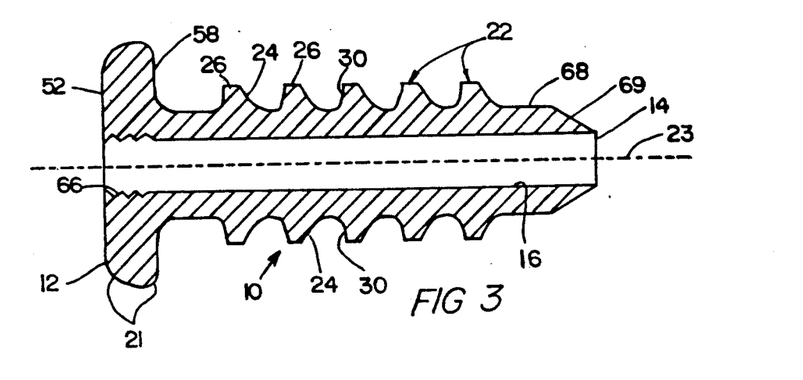
FIG. 3 is a section taken along lines 3—3 of FIG. 2.

The bore 16 has internal threads 66 adjacent securing head 20 to mount the tack 10 onto an impactor or applicator as discussed hereinafter.

Figure 1:
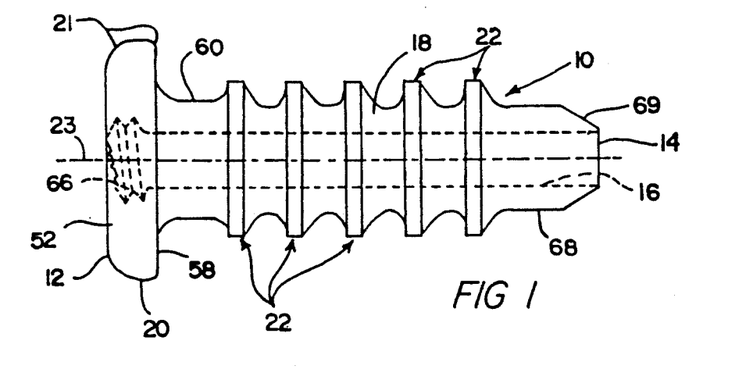
FIG. 1 is a side view of a bioabsorbable tack according to the present invention.

At the distal end 14 of the tack 10, the most distal annular rib 22 has a forward facing surface 24 arcuately joining a distal root cylindrical section 68 that terminates at a distal frusto-conical section 69 extending to the distal tack end 14, the distal frusto-conical section 69 being disposed at an angle to the longitudinal axis 23 of approximately 30°. The length of the tack 10 from the proximal end 12 to the distal end 14 is approximately 0.570 inches, and the proximal rib edge 32 of the most distal annular rib 22 is spaced from the distal tack end 14 by approximately 0.154 inches.

The tack 10, as shown, has five annular ribs 22; however, the number of annular ribs 22 can be varied dependent upon the tissue and bone where the tack is to be applied. To this end, the dimensions set forth above are exemplary only, and the dimensions can vary so long as the tack retains the structural integrity to withstand longitudinal insertion forces, provide a secure fastening to bone and resist backing out as described below.

Tack 10 is made from a bioabsorbable or biodegradable polymer or copolymer of a type selected in accordance with the desired absorbtion or degradation time. That time, in turn, depends upon the anticipated healing time for the reattachment of soft tissue to the bone or other tissue which is the subject of the surgical procedure. Known biodegradable polymers and copolymers range in degradation time from about three months for polyglycolide to about forty-eight months for polyglutamic-coleucine. A common biodegradable polymer used in absorbable sutures and the like is poly(L-lactide) which has a degradation time of about twelve to eighteen months.

As discussed briefly above, the actual material used for tack 10 is preferably an absorbable copolymer derived from glycolic and lactic acids, such as a synthetic polyester chemically similar to other commercial available glycolide and lactide copolymers. Glycolide and lactide, in vivo, degrade and absorb by hydrolysis into lactic acid and glycolic acid which are then metabolized by the body.

The table set forth below lists polymers (and copolymers and terpolymers thereof) which are useful for the biodegradable material employed for the tack 10 of the present invention. These polymers are all biodegradable into water-soluble non-toxic materials which can be eliminated by the body. All are well known for use in humans and their safety has been demonstrated and approved by the U.S. Food and Drug Administration. Although these polymers are normally linear, cross linked resins can be prepared from these materials by those skilled in the art.

TABLE

| Polymer |
| --- |
| Polycaprolactone |
| Poly(L-lactide) |
| Poly(DL-lactide) |
| Polyglycolide |
| 95:5 Poly (DL-lactide-co-glycolide) |
| 90:10 Poly(DL-lactide-co-glycolide) |
| 85:15 Poly(DL-lactide-co-glycolide) |
| 75:25 Poly(DL-lactide-co-glycolide) |
| 50:50 Poly(DL-lactide-co-glycolide) |
| 90:10 Poly (DL-lactide-co-caprolactone) |
| 75:25 Poly (DL-lactide-co-caprolactone) |
| 50:50 Poly (DL-lactide-co-caprolactone) |
| Polydioxanone |
| Polyesteramides |
| Copolyoxalates |
| Polycarbonates |
| Poly(glutamic-co-leucine) |

The tack 10 of the present invention has been designed for application by a longitudinal, axial force rather than by rotation as required for screws. The forward facing surface 28 is designed to push granulated bone radially away during insertion of the tack into bone, and the springy nature of the bone causes the bone to move back into the grooved areas defined between the annular ribs 22 on the stem 18 thus securing the tack in the bone and creating substantial resistance against rearward movement of the inserted tack 10. To assure the structural integrity of the tack during insertion and while in place, the ratio of the length of the maximum diameter cylindrical section 26 to the distance between the minimum and maximum cylindrical sections is preferably in the range of from 0.8 to 1 through 0.4 to 1 and is preferred to be 0.6 to 1. By constructing the ribs within this range, the ribs will resist breaking during insertion while retaining semi-rigidity to facilitate insertion with minimal flexing and to be rigidly held in the bone to resist backing out. The preferred ratio of the root cylinder diameter to the maximum cylinder diameter is approximately 2:3 and combines with the rib height and rib spacing to secure the tack in bone.

The tack 10 will be described hereinafter for use in arthroscopic surgery for the repair of soft tissue which has separated from the bone, particularly in the shoulder area; however, as previously discussed, the tack has utilization for repairing other bodily tissue by arthroscopic or open surgical procedures.

Figures 5, 6:
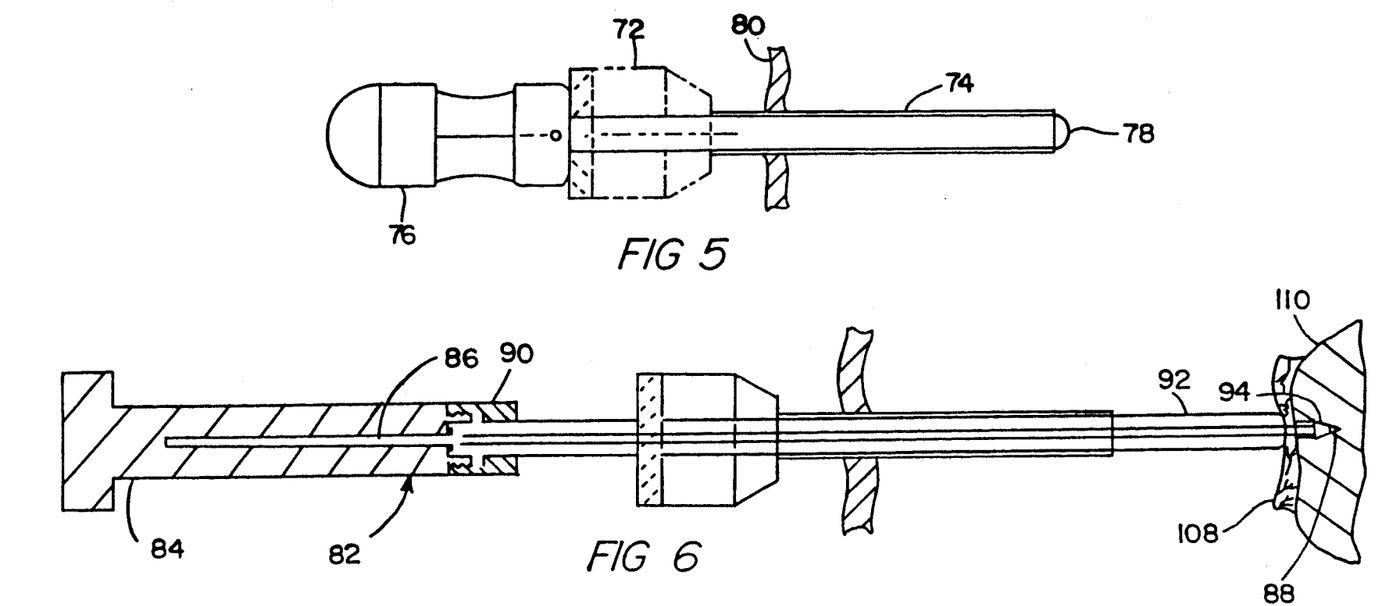
FIG. 5 is a side view of a cannula containing an obturator inserted in the body for deploying the tack according to the present invention.
FIG. 6 is a side view of an inserter and trocar wire for engaging and orienting tissue relative to bone.
Figure 7:
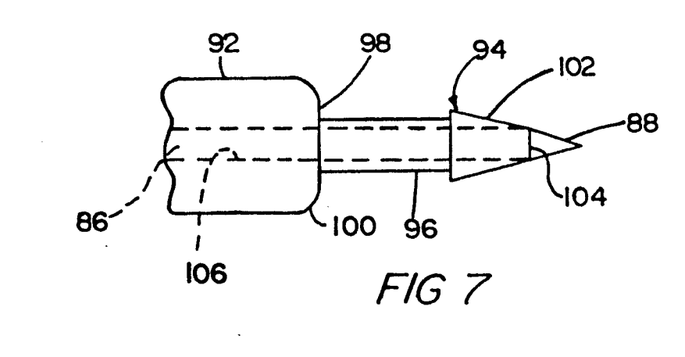
FIG. 7 is a broken side view of the distal end of the inserter.

Use of the tack 10 to secure soft tissue to bone and instruments for applying the tack are illustrated in FIGS. 5-11. Initially, a conventional insertion cannula having a hub 72 and a sleeve 74 with a removable obturator 76 having a blunt distal end 78 received in the cannula is inserted through the skin 80 by a standard surgical procedure, such as an incision at a position where tissue attachment to bone is to take place. The obturator is then removed from the insertion cannula, and an inserter 82, as shown in FIG. 6, is introduced into the insertion cannula. The inserter 82 includes a handle 84 having an axial bore 86 receiving a proximal end of a trocar wire 86 having a sharp distal end 88. The handle 84 threadedly engages a hub 90 secured to the proximal end of an elongate cylindrical member 92 of a size to pass freely through sleeve 74, and member 92 terminates distally at a barb 94 having, as shown in FIG. 7, a narrow hollow neck 96 extending from a distal surface 98 having a rounded shoulder 100, the neck supporting a frusto-conical tip 102 having an open distal end 104 and a diameter at the proximal end 106 thereof greater than the diameter of neck 96 to form an edge for engaging tissue in barb-like fashion. A longitudinal axial passage 106 passes through member 92 and barb 94 allowing trocar wire 86 to pass therethrough with sharp end 88 extending through open distal end 104, the sharp end 88 having a conical angular shape to be a smooth extension of barb 102. The inserter 82 is used to hook soft tissue 108 to be attached to bone 110 by penetrating the tissue with barb 94 and the sharp distal end 88 of the trocar wire; and, after the tissue 108 is hooked, the tissue is moved to the bone attachment site where the sharp distal end of the trocar wire and the barb are hammered into the bone by impacting handle 84 to the position shown in FIG. 6. The distal surface 98 will not cut through the tissue 108 due to the rounder shoulder 100; and, thus, the surgeon can safely hammer the inserter tip into the bone.

Figure 8:
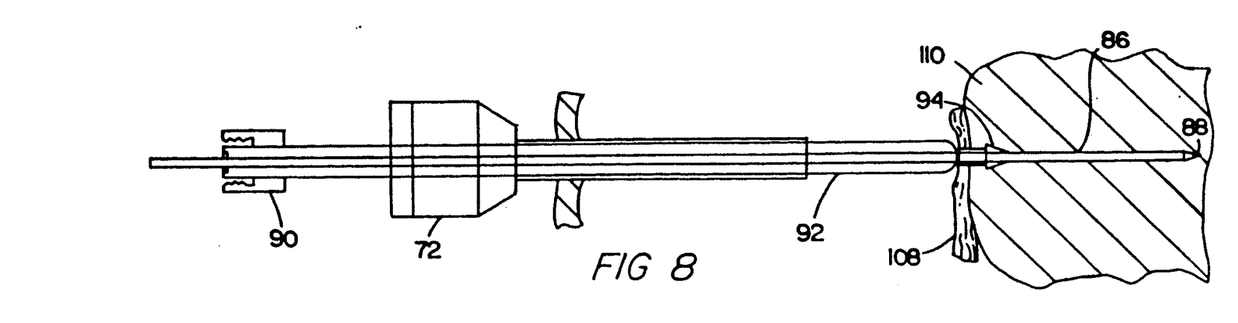
FIG. 8 is a side view showing driving of the trocar wire into the bone.
Figure 9:
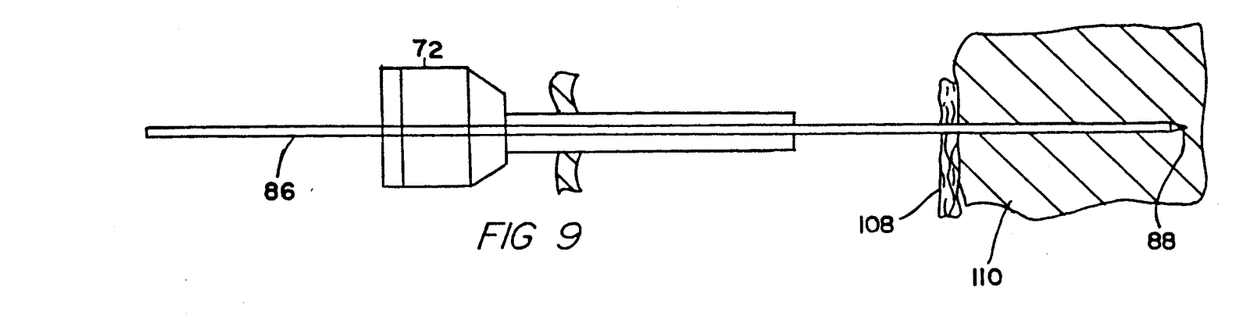
FIG. 9 is a side view with the inserter removed.

After the inserter tip is initially positioned in the bone as shown in FIG. 6, the handle 84 is unscrewed from hub 90, and a conventional wire driver, such as the C-WIRE SERTER manufactured by Concept, Inc., is used to drive the trocar wire 86 further into the bone 110 to a desired distance as shown in FIG. 8. After the trocar wire is driven into the bone, the inserter is removed leaving only the trocar wire in place, as shown in FIG. 9, the tissue remaining in place while the barb is pulled therethrough.

Figure 10:
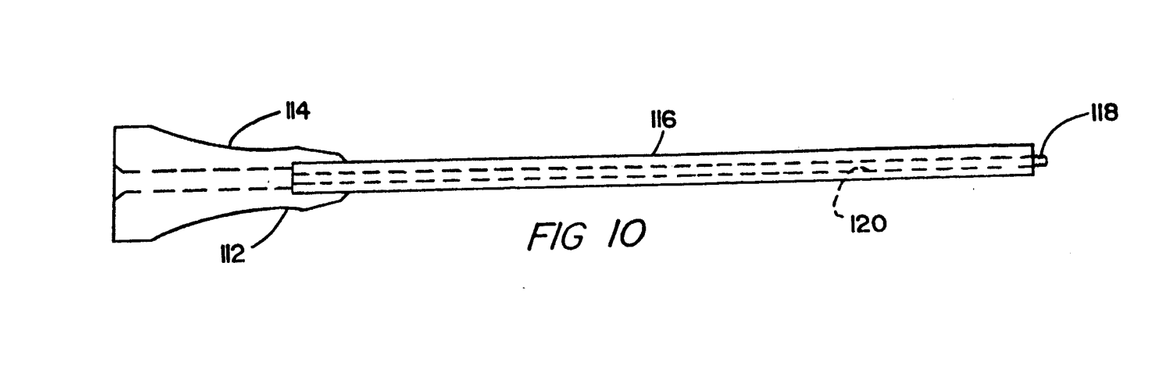
FIG. 10 is a side view of an impactor for mounting the tack.
Figure 11:
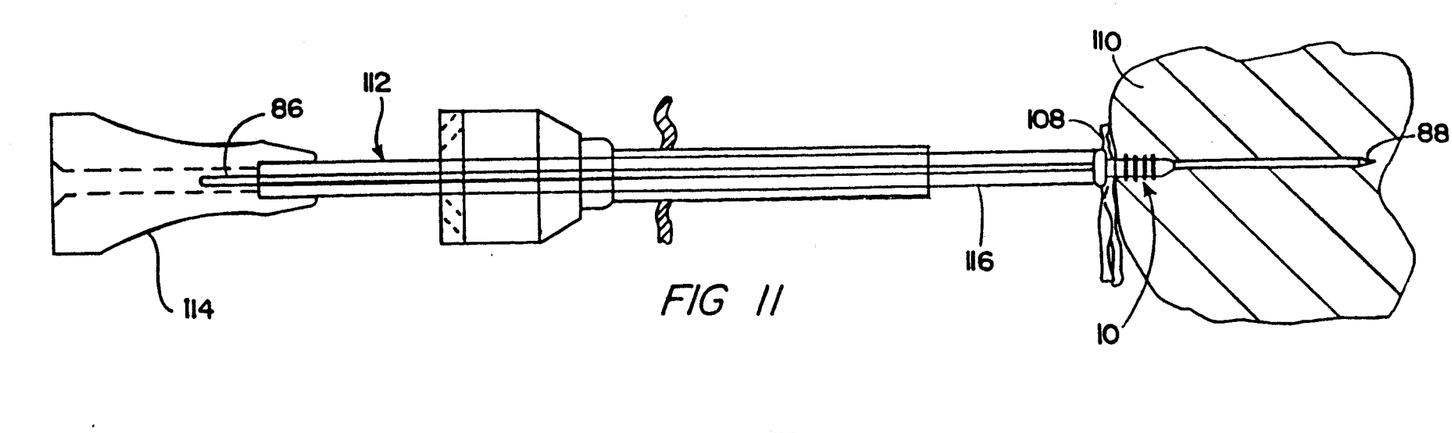
FIG. 11 is a side view showing insertion of the tack into the bone with the impactor.

The tack 10 is now mounted on an impactor 112 shown in FIG. 10 including a handle 114 and an elongate cylindrical member 116 secured in the handle and having an externally threaded distal end 118. A longitudinal passage 120 extends through handle 114, cylindrical member 116 and threaded distal end 118 such that the impactor 112 is cannulated to receive the trocar wire 86. The tack 10, which is also cannulated as described above, is threaded onto distal end 118 via internal threads 66 at the proximal end of the tack. With the tack threadedly mounted on the impactor 112, the tack and impactor are moved over the trocar wire 86 to the attachment site, as shown in FIG. 11, and the tack is hammered into the bone by impacting handle 114. As previously described, the tack is constructed in a manner to withstand the forces resulting from the longitudinal insertion thereof, and the trocar wire passing through the tack coupled with the threaded distal end 118 of the impactor being disposed within the tack head further reinforce the tack such that, even though the tack is made of a bioabsorbable material having less structural rigidity than metal, the tack can be inserted in the bone without breakage or undesirable deformation.

Figure 12:
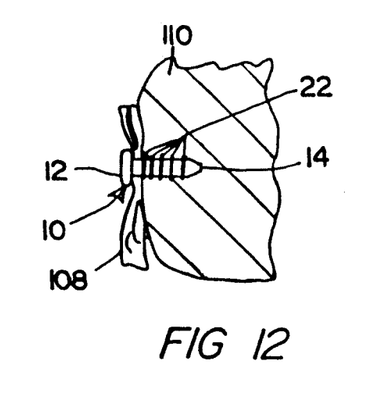
FIG. 12 is a side view showing the tack attaching the tissue to the bone.

After the tack has been inserted as shown in FIG. 11, the impactor 112 is rotated to unthread the tack therefrom and the impactor is then removed. The wire driver is then coupled to the proximal end of the trocar wire and used to pull the trocar wire out. The cannula 72 is now removed, and the incision closed leaving the tack in place attaching the tissue to the bone, as shown in FIG. 12. As previously described, the degradation time of the tack will be greater than the time required for the tissue to attach to the bone such that healing will be complete before the tack loses its ability to hold the tissue in place.

Inasmuch as the present invention is subject to many variations, modifications and changes in detail, it is intended that the subject matter discussed above and shown in the accompanying drawings be interpreted as illustrative and not in a limiting sense.

What is claimed:

1. A surgical system for attaching bodily tissue in vivo to bone at an attachment site, said system comprising:
   a trocar wire having a sharp distal end;
   inserter means for inserting the distal end of the trocar wire through the tissue and into the bone at the attachment site to maintain the tissue adjacent the attachment site;
   a bioabsorbable tack having a proximal end and a distal end and a bore extending longitudinally therethrough of sufficiently large cross-section to receive said trocar wire therein;
   impactor means having a proximal end and a distal end and a longitudinal passage extending therethrough of sufficiently large cross-section to receive said trocar wire therein;
   securing means for removably securing said tack to said distal end of said impactor means with said trocar wire extending through said longitudinal passage and said longitudinal bore, whereby said impactor and said tack are movable along said trocar wire to position the distal end of said tack adjacent said tissue at the attachment site;
   wherein said impactor means includes means for inserting said tack through the tissue and into the bore to engage the bone and retain the tissue against the bone;
   whereby upon disengaging the impactor from the tack, the impactor and the trocar wire may be retracted from the tissue without removing the tack.

2. The system according to claim 1 wherein said securing means comprises means for threadedly engaging said distal end of said impactor to said proximal end of said tack.

3. The system according to claim 1 wherein said securing means comprises means for engaging said distal end of said impactor to said tack at a location inside said longitudinal bore.

4. The system according to claim 3 wherein said securing means comprises a first threaded section of said longitudinal bore and a second threaded section of said impactor, said first and second threaded sections being selectively engageable to secure said impactor to said tack.

5. The system according to claim 4 further comprising a cannula adapted to project through an incision toward the surgical site and configured to receive said impactor means and said inserter means with the trocar wire in longitudinally movable relation to direct said inserter means and said impactor means toward the attachment site.

6. The system according to claim 1 wherein said tack includes a head disposed at said proximal end of said tack, and a plurality of discrete axially spaced annular ribs disposed in successive longitudinal positions along said tack intermediate said proximal and distal ends.

7. The system according to claim 6 wherein said impactor means is responsive to hammer blows applied thereto for driving said tack through the tissue and into the bone.

8. A surgical system for attaching bodily tissue in vivo to bone at an attachment site, said system comprising:
   a trocar wire having a sharp distal end;
   an inserter for inserting said distal end of said trocar wire through the tissue and into the bone at the attachment site to maintain the tissue adjacent the attachment site;
   a bioabsorbable tack having a proximal end and a distal end and a bore extending longitudinally therethrough of sufficiently large cross-section to receive said trocar wire therein;
   an impactor having a proximal end and a distal end and a longitudinal passage extending therethrough of sufficiently large cross-section to receive said trocar wire therein;
   securing means for removably securing said tack to said distal end of said impactor with said trocar wire extending through said longitudinal passage and said longitudinal bore, whereby said impactor and said tack are movable along said trocar wire to position said distal end of said tack adjacent the tissue at the attachment site;
   wherein said impactor includes means for inserting said tack through the tissue and into the bore to engage the bone and retain the tissue against the bone;
   whereby upon disengaging said impactor from said tack, said impactor and said trocar wire may be retracted from the tissue without removing the tack;
   wherein said inserter comprises:
   an elongate member having a proximal end, a distal end and a longitudinal passage therethrough; and
   a barb disposed at said distal end of said elongate member for engaging the tissue in barb-like fashion and having a longitudinal passage therethrough aligned with said passage through said elongate member whereby said trocar wire can pass through said passages in said elongate member and barb.

9. The system as recited in claim 8 wherein said barb means further includes a neck extending from the distal end of said elongate member and a frusto-conical tip extending from said neck, said tip having an open distal end and a proximal end with a diameter greater than a transverse dimension of said neck to define an edge for engaging the tissue.

10. The system as recited in claim 9 wherein the distal end of said elongate member has a rounded shoulder to prevent said distal end of said elongate member from cutting through the tissue.

11. The system as recited in claim 10 further comprising a handle removably secured to the proximal end of said elongate member, and wherein said trocar wire has a proxial end received in said handle.

12. A surgical system for attaching bodily tissue in vivo to bone at an attachment site, said system comprising:
   a trocar wire having a sharp distal end;

an inserter for inserting said distal end of said trocar wire through the tissue and into the bone at the attachment site to maintain the tissue adjacent the attachment site;

a tack made up of bioabsorbable material for attaching the bodily tissue to the bone at the attachment site to permit healing in vivo, said tack including a stem with a proximal end and a distal end, said tack further including a head disposed at said proximal end of said stem, a bore extending longitudinally through said tack and having a sufficiently large cross-section to receive said trocar wire therein, and a plurality of discrete axially spaced annular ribs disposed at successive longitudinal positions along said stem intermediate said proximal and distal ends;

an impactor having a proximal end responsive to hammer blows, a distal end for mounting said tack and a longitudinal passage extending therethrough of sufficiently large cross-section to receive said trocar wire therein, said impactor being operative to move said tack to the attachment site and to apply longitudinal forces from the hammer blows to said tack to drive said tack through said bodily tissue and into said bone; and releasable securing means located in said bore of said tack for securing said distal end of said impactor in said bore with said longitudinal passage of said impactor in axial alignment with said bore of said tack and with said trocar wire extending through said longitudinal passage and said bore, said releasable securing means holding said tack on said impactor during movement of said tack to the attachment site;

whereby upon disengaging said impactor from said tack, said impactor and said trocar wire may be retracted from the tissue without removing said tack.

13. The system according to claim 12 wherein said securing means includes external threads disposed on said distal end of said impactor and internal threads disposed in said bore adjacent said head of said tack.

14. The system according to claim 13 further comprising a cannula adapted to project through an incision toward the attachment site and configured to receive said impactor and said inserter with the trocar wire in longitudinally movable relation to direct said inserter and said impactor toward the attachment site.

15. The system according to claim 12 wherein said inserter means comprises:

an elongate member having a proximal end, a distal end and a longitudinal passage therethrough; and barb means disposed at said distal end of said elongate member for engaging the bodily tissue in barb-like fashion and having a longitudinal passage therethrough aligned with said passage through the elongate member, whereby the trocar wire can pass through the passages in the elongate member and barb means.

16. The system according to claim 12 wherein said barb means further includes a neck extending from the distal end of said elongate member and a frusto-conical tip extending from said neck, said tip having an open distal end and a proximal end with a diameter greater than a transverse dimension of said neck to define an edge for engaging the bodily tissue.

17. The system as recited in claim 16 wherein the distal end of said elongate member has a rounded shoulder to prevent said distal end of said elongate member from cutting through the tissue.

18. The system as recited in claim 17 further comprising a handle removably secured to the proximal end of said elongate member, and wherein said trocar wire has a proximal end received in said handle.

* * * * *

UNITED STATES PATENT AND TRADEMARK OFFICE
CERTIFICATE OF CORRECTION

PATENT NO. : 5,203,784
DATED : April 20, 1993
INVENTOR(S) : Randall D. Ross et al It is certified that error appears in the above-identified patent and that said Letters Patent is hereby corrected as shown below:

Correct the title of the patent to read --System and Method of Attaching Bodily Tissue to Bone--.

Column 1, line 51, delete "with" and replace with --without--.

Column 1, line 61, delete "a" and replace with --an--.

Column 4, line 13, after "5", insert --°--.

Column 4, lines 61, 62, 63 and 64, delete in their entirety.

Column 4, line 65, delete "tack 10 is preferably" and substitute therefor --sutures is--.

Column 5, line 3, after "body.", add --The preferred material for tack 10 is poly (L-lactide) which has a degradation time of about twelve to eighteen months.--

Column 5, in the Table, after "50:50 Poly (DL-lactide-co-caprolactone)" insert --95:5 - 5:50 Poly (L-lactide-co-caprolactone)--

Column 5, line 36, delete "granulated".

UNITED STATES PATENT AND TRADEMARK OFFICE
CERTIFICATE OF CORRECTION

PATENT NO. : 5,203,784

DATED : April 20, 1993

INVENTOR(S) : Randall D. Ross et al

It is certified that error appears in the above-identified patent and that said Letters Patent is hereby corrected as shown below:

Column 5, line 45, delete "section" and replace with --sections--.

Column 6, line 30, delete "rounder" and replace with --rounded--.

Column 7, line 3, after incision, insert --is--.

Signed and Sealed this

Eighth Day of March, 1994

Attest:

BRUCE LEHMAN

Attesting Officer

Commissioner of Patents and Trademarks